(12) United States Patent
Axelgaard

(10) Patent No.: US 6,418,333 B1
(45) Date of Patent: Jul. 9, 2002

(54) FLOATING ELECTRODE

(75) Inventor: Jens Axelgaard, Fallbrook, CA (US)

(73) Assignee: Axelgaard Manufacturing Co., Ltd., Fallbrook, CA (US)

( * ) Notice: Subject to any disclaimer, the term of this patent is extended or adjusted under 35 U.S.C. 154(b) by 0 days.

(21) Appl. No.: 09/676,823

(22) Filed: Oct. 2, 2000

(51) Int. Cl.⁷ .................................................. A61B 5/04
(52) U.S. Cl. ...................... 600/391; 600/392; 600/395; 600/397; 607/149; 607/152; 604/20
(58) Field of Search ............................... 600/372, 386, 600/391–393, 395, 397; 607/149, 152, 153; 604/20

(56) References Cited

U.S. PATENT DOCUMENTS

| | | | | |
|---|---|---|---|---|
| 3,993,049 A | * | 11/1976 | Kater | 600/391 |
| 4,066,078 A | * | 1/1978 | Berg | 600/391 |
| 4,458,696 A | * | 7/1984 | Larimore | 600/391 |
| 4,515,162 A | * | 5/1985 | Yamamoto et al. | 600/391 |
| 4,736,752 A | * | 4/1988 | Munck et al. | 607/152 |
| 6,263,226 B1 | * | 7/2001 | Axelgaard et al. | 600/391 |

* cited by examiner

*Primary Examiner*—Lee Cohen
(74) *Attorney, Agent, or Firm*—Walter A. Hackler

(57) ABSTRACT

A medical electrode includes a first conductive polymerizable gel layer for electrically coupling the electrode to a body and a flexible porous electrical conductor disposed on the first gel layer. A second conductive polymerizable gel layer disposed on the flexible porous electrical conductor and polymerized with the first layer through the porous conductor. An electrical connector disposed in connect with the second gel layer enables the electrical connection to an outside power source, or monitoring device, and an insulative backing is adhered to the second gel layer to prevent inadvertent contact therewith.

29 Claims, 2 Drawing Sheets

FLOATING ELECTRODE

The present invention generally relates to electrodes and, more particularly, to medical electrodes for transcutaneous stimulation of nerves and/or muscles or monitoring of biological or physiological electrical potentials in a body.

Transcutaneous electrical nerve stimulation electrodes are useful in pain control while electrical muscle stimulation electrodes are useful in maintaining and developing tissue. Stimulating electrodes of this type may also incorporate a medicament for iontophoreses, that is, the introduction of a topically applied physiologically active ion into the epidermis and mucus membranes of the body by the use of electrical current.

Monitoring electrodes are, used, for example, in conjunction with monitoring devices to produce, for example, electroencephalograms (EEG), electromyograms (EMG) and electrocardiographs (ECG).

Because of the curved nature of the epidermis layer on to which the electrodes are applied, the flexibility of the electrode is of paramount importance.

In additions, physical and electrical stability of the electrodes must be maintained over long periods of application. In that regard, a specific difficulty in heretofore developed electrodes manifest itself in the electrical connection of the electrode to an outside power source or monitoring device. That is, some type of lead wire must be connected to the electrode and maintain constant electrically continuity between the lead wire and the electrode. In the case of stimulation electrodes, electrical continuity is required to provide constant uniform current distribution. Disruption of current, i.e., an abrupt connect/disconnect occurrence, can cause a startling effect on a body. In the case of monitoring electrodes, electrical continuity is required for uniform sensing of electrical potential. Interruption of electrical continuity in monitoring electrodes may result in "false alarms", such as spurious electrical output, or open circuit conditions in which information flow is disrupted.

Typically the lead wire is soldered, welded, cemented or otherwise held in direct contact with a highly conductive element of an electrode such as a metallic foil, mesh or conductive woven fabrics or the like. These conductive elements are coupled to a body though a conductive gel and covered with a non-conductive backing to prevent undesired contact from a reverse side of the electrode with the conductive element.

This necessity of direct contact between a lead wire and the conductive element has limited the performance of medical electrodes to this date.

The present invention provides for an electrode having a conductive element which makes no direct contact to an electrical lead wire or connector thus eliminating problems associated with heretofore required interconnection.

SUMMARY OF THE INVENTION

A medical electrode in accordance with the present invention, generally includes a first conductive polymerizable gel layer for electrically coupling the electrode to a body along with a flexible electrical conductor disposed on the first gel layer. The electrical conductor may be a conductive fabric or sheet comprised of conductive and non-conductive elements. Other combinations are also contemplated as part of the present invention, as, for example, a sheet with low conductivity with a highly conductive layer disposed thereon.

A second conductive polymerizable gel layer is provided and disposed on the flexible electrical conductor to suspend or float the conductor between the first and second gels.

In one embodiment, the conductor is porous and importantly, the first and second gel layers are polymerized with one another through the porous conductor.

This polymerization through the flexible porous electrical conductor is preferred in order to not only secure the flexible porous electrical conductor within a unitary gel consisting of the first and second layers, but also to provide intimate electrical contact between the flexible porous electrical conductor and the gel.

It should be appreciated that the flexible porous electrical conductor is not contacted by any other medium but the gel and hence the conductor can be considered as "floating" within the gel.

In addition, the flexible porous electrical conductor provides structural integrity to the gel. Because it is laminated or bonded therein through the polymerization of the gels and embedded therein, the flexible porous electrical conductor provides structural integrity to the gel.

An electrical connector is provided and disposed in contact with the second gel layer and insulative backing is adhered to the second gel layer. In this manner, initial electrical connection to the flexible porous electrical conductor is made through the gel.

In one embodiment of the present invention, the electrical connector extends through the backing for electrical access thereto. This structure enables secure fastening of the electrical connector, which may be a snap connector, because it is physically surrounded by the backing.

In order to enhance the electrical coupling between the electrical conductor and the connector, the second gel layer may be. more electrically conductive than the first gel layer. In this manner the second gel layer provides for enhanced electrical distribution across the conductor and the first layer thereafter couples this evenly distributed current profile to the body.

More particularly, the flexible porous conductor may comprise a non-electrically conductive sheet with an electrical grid disposed thereon. Preferably the electrical grid comprises an electrically conductive ink pattern printed on the non-electrically conductive sheet.

In one embodiment of the present invention, suitable for stimulation electrodes, the ink pattern includes a perimeter with interconnecting ink lines with the perimeter being set apart from edges of the non-electrically conducted sheet. This configuration provides a roll off of electrical current from the edges of the electrode.

In another embodiment, suitable for monitoring electrodes, the conductor may have dimensions substantially equal to the first and second gel dimensions. In this instance greater electrode monitoring sensitivity is afforded the electrode.

In yet another embodiment of the present invention, the electrical contact may include a lead wire in contact with a second gel layer and a second conductive grid may be utilized to enhance the electrical coupling therebetween.

Further embodiments of medical electrodes in accordance with the present invention include a first conductive polymerizable, gel layer for electrically coupling the electrode to a body and a medicament containing conductive polymerizable gel layer polymerized or bonded to the first gel layer.

A flexible porous electrical conductor is disposed on the medicament containing gel and a second conductive polymerizable gel layer is disposed on a flexible porous electrical conductor and polymerized with the medicament containing gel through the porous conductor. An electrical connector is disposed in contact with the second gel layer and an insulative backing is adhered to the second gel layer.

BRIEF DESCRIPTION OF THE DRAWINGS

The present invention may be more clearly understood with references to the following detailed description, in conjunction with the appended drawings of which.

DETAILED DESCRIPTION

Figure 1:
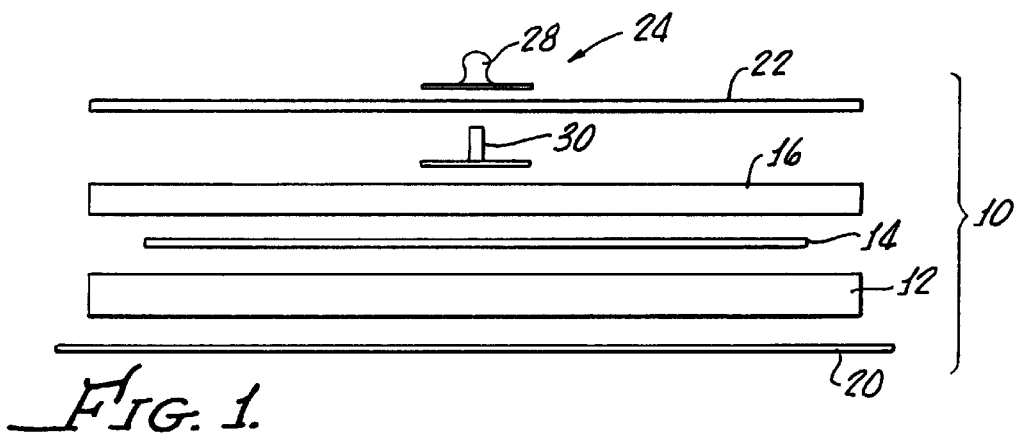
FIG. 1 is an exploded side view of electrode in accordance with the present invention generally showing first and second polymerizable conductive gel layers along with a flexible electrical conductor to be polymerized therebetween, an electrical connector, backing sheet and a release layer for contacting the first gel layer before use.
Figure 2:
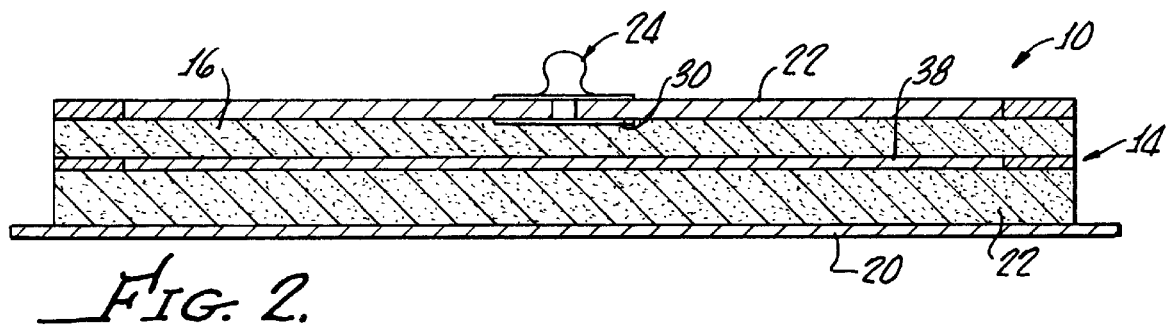
FIG. 2 is a cross-sectional view of the electrode as shown in FIG. 1 showing an assembled electrode with the flexible electrical conductor floating, or suspended, within the first and second gel layers.

With references to FIGS. 1 and 2, there is shown a medical electrode 10 in accordance with the present invention which includes a first conductive polymerizable gel layer 12 for electrically coupling the electrode 10 to a body (not shown) and a flexible electrical conductor 14 disposed on the first gel layer 12. The conductor 14 may be an impervious foil or the like, or a porous media as will be hereinafter described.

A second conductive polymerizable gel layer 16 is disposed on the flexible electrical conductor 14 in order to embed the conductor 14 within the gel layers 12, 16. When an impervious foil is utilized, the layers 12, 16 are laminated or bonded thereto in order to float the conductor 14 between the layers 12, 16. A porous conductor 14 is held or bonded between the layers 12, 16 by polymerization through the porous conductor 14 as shown in FIG. 2.

The gel layers 12, 16 may be of any suitable type but preferably polymerizable polymers as set forth in U.S. Pat. Nos. 5,868,136, 6,038,464 and 6,115,625 and U.S. Ser. No. 09/428,196 filed Oct. 27, 1999 entitled MEDICAL ELECTRODE COMPRESS. These patent are incorporated in their entirety herewith, including all of the drawings and specifications in order to describe the type of gels which are suitable for use in the present invention. It should be appreciated that while only two layers 12, 16 have been discussed hereinabove, additional layers (not shown) which may be utilized, are considered to be part of the present invention. Such layers are discussed in the patents incorporated by reference herein.

The gels may be polymerized together in any conventional manner including heat, UV light, or any other method to insure polymerization of both the layers 12, 16 to each other and through the conductor 14 in order to embed, float, or suspend the conductor 14 between the layers 12, 16.

In addition, the conductor 14, which will be described in greater detail hereinafter, provides for mechanical strength and integrity for handling of the polymerized gel layers 12, 16.

A release carrier 20 which may be of any suitable type is provided for covering the gel 12 prior to application of the electrode 10 to a body (not shown). In addition, as shown in FIGS. 1 and 2, a non-conductive backing 22 is applied over the gel layer 16 in order to prevent. undesired contact therewith.

As shown in FIGS. 1 and 2, a snap connector 24 including a snap stud 28 and eyelet 30 extends through the backing 22 which provides for secure mechanical linkage with the electrode 10 and importantly the electrical contact with the gel 16.

It is important to appreciate that the electrode construction in accordance with the present invention features a conductor 14 which has no mechanical electrical connection thereto. All electrical connection with the conductor 14 is made through the gel 16 from the snap connector 24 and through the gel 12 to a body.

Accordingly, there is no mechanical structural contact between the snap connector 24 and the conductor 14. Because the gel 16 is flexible and the snap connector 24 is secured within the backing 22, rough handling of the snap connector will not cause any separation in electrical contact or intermittent poor electrical conduction between the snap connector and the conductor 14 by, for example, pulling on an electrical wire (not shown) connected or snapped to the snap connector 24.

This feature overcomes a number of drawbacks with prior art. connectors in which the electrode conductor mechanically and physically touches an electrical lead wire contact, the latter being necessary for connection to an outside power source or monitoring device.

Figure 3:
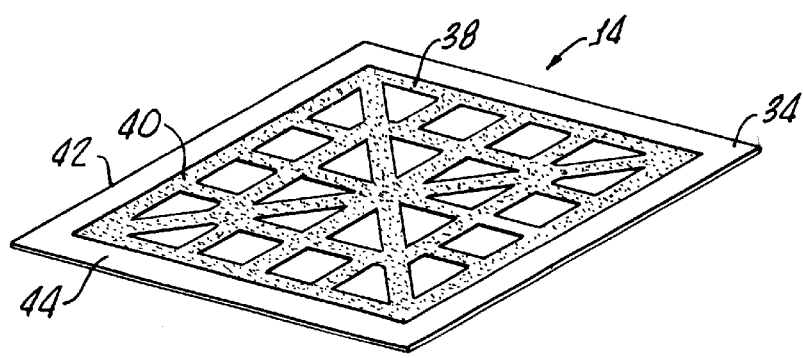
FIG. 3 is a perspective view of the flexible porous electrical conductor showing in greater detail a conductive ink pattern on a non-conductive porous substrate sheet.

Polymerization of the gel layers 12, 16 through the conductor 14, is afforded through the use of a blown porous polyester material 34 which may have a thickness of between about 1 mil and about 10 mils, preferably about 5 mils, and is available from Reemay, Inc. of Old Hickory, Tenn. This polyester is porous and non-conductive. Conductivity is provided and controlled by an electrical grid 38 which is preferably printed on the polyester 34 with a conductive ink 40, see FIG. 3.

The conductive ink grid 38 may be of suitable type and when applied to the polyester 34 does not alter the porosity thereof and accordingly, the gel layers 12, 16 may be polymerized, not only through the polyester 34 but through the ink grid 38 disposed on the polyester 34.

The technique of utilizing an ink grid 38 of specific patterns to control current is set forth in U.S. Pat. Nos. 4,736,752, 5,843,155, 5,904,712 and 6,038,485. These patents are to be incorporated by these specific reference thereto in their entirety including all Figures and specifications in order to describe arrays of conductive ink patterns, or grid 38, which may be utilized in the present invention.

Preferably for a stimulation electrode 10, the ink grid pattern 38 includes a perimeter 40 which is set apart from an edge 42 of the non-electrically conductive polyester sheet 34 to provide a setback 44 in order to prevent any shunting of electrical current to a body (not shown).

The gel layers 12, 16 may have thicknesses of about 25 mils and 10 mils respectively. However, thickness of up to 100 mils may be utilized. Thus, the electrode 10 may have a very thin profile and enhanced flexibility. Furthermore, in order to control the conductivity of the electrode 10, the second gel layer 16 may be more electrically conductive than the first gel layer 12. Control of conductivity is set forth in the hereinabove patents which have been incorporated herewith by specific references thereto. Specifically, the conductivity of the second gel is less than about 1000 ohm-cm and the conductivity of the first gel is less than about 2000 ohm-cm.

Figure 4:
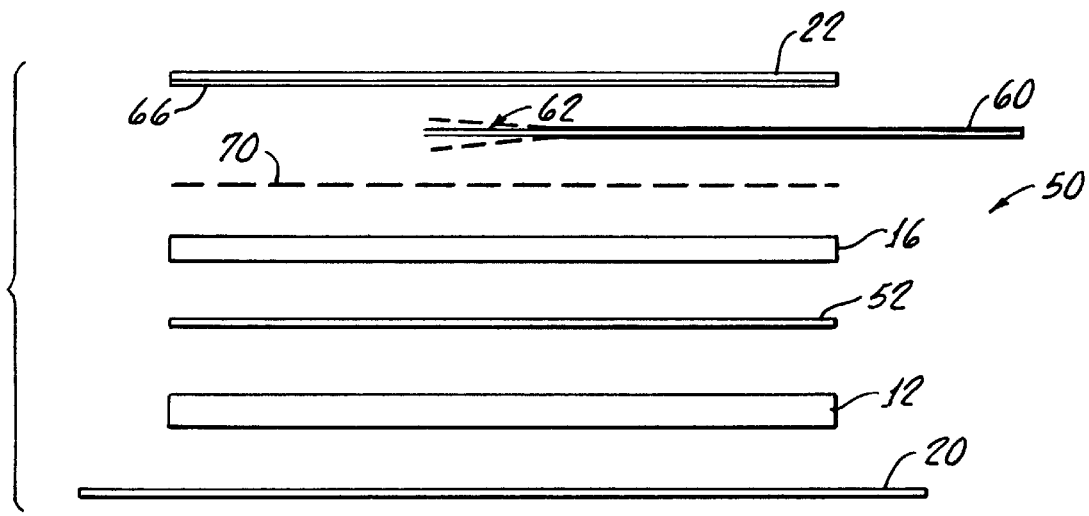
FIG. 4 is an exploded side view of an alternative embodiment of the present invention which utilizes an electrical lead for contact with an outside electrical source (not shown)

With reference to FIG. 4, there is shown an alternate embodiment electrode 50 in accordance with the present invention suitable both for electrical stimulation and for monitoring of electrical potentials from a body. Common reference characters refer to structural components which are substantially equivalent to the embodiment 10 shown in FIGS. 1–3.

Electrode 50 incorporates the first and the second conductive polymerizable gel layers of 12, 16 along with an impervious flexible electrical conductor 52, backing 22 and release carrier 20.

In this embodiment 50 the conductor may be a conductive film, such as carbon, or a conductive mesh flood coated with a carbon, Ag or AgCl ink or any combination thereof. A Combination of a conductive film with Ag/AgCl ink on top thereof will prevent any migration of Ag/AgCl into the body (not shown). This combination may also be used in the embodiment 10 hereinabove discussed.

An important feature of the electrode 50 shown in FIG. 4 is the utilization of a lead wire 60 as an electrical connector for contacting the second gel layer 16. When utilized, the lead wire 60 provides the electrode 50 with an extremely thin cross-section, which importantly includes no bulges or bumps, as is the case when snap connector 24 (see FIGS. 1 and 2), is utilized. Thus, the long term use of the electrode 50 may be more comfortable to a user (not shown), particularly when body weight is pressed against the electrode 50 during use.

The lead wire 60 may include wire strands 62 which may be adhered to the backing 22 by an adhesive layer 66.

Alternatively, the lead 60 and wire 62 may be adhered to the gel layer 16 by the adhesiveness of the gel layer itself. When the lead 60 and wire 62 are adhered to both the gel layer 16 and backing 22, a secure mechanical connection is afforded with the electrode 50.

Importantly, as with the embodiment 10, utilizing a snap connector, because the lead 60 and wire 62. do not directly contact the conductor 14, tugging or pulling on the lead 60, will not cause any disruption in the contact between the lead wire 62 and conductor 14 because such contact is made though the flexible conductive gel 16. Accordingly, no disruption in the electrical conductivity occurs through rough handling of the electrode by way of a body contact and inadvertent pulling of the lead 60.

To further reinforce the mechanical anchoring of the leadwire a grid 70 may be provided as shown in FIG. 4. This grid 70 should be flexible and may be a mesh, foil, or other conductive medium. Further, if the grid 70 is electrically conductive, such as for example a carbon coated media, electrical contact between the wire 62 and the gel 16 is also insured. It should also be appreciated that such a grid 70 could be used in the electrode embodiment 10 between the snap connector eyelet 30 and the conductive gel layer 16.

Figure 5:
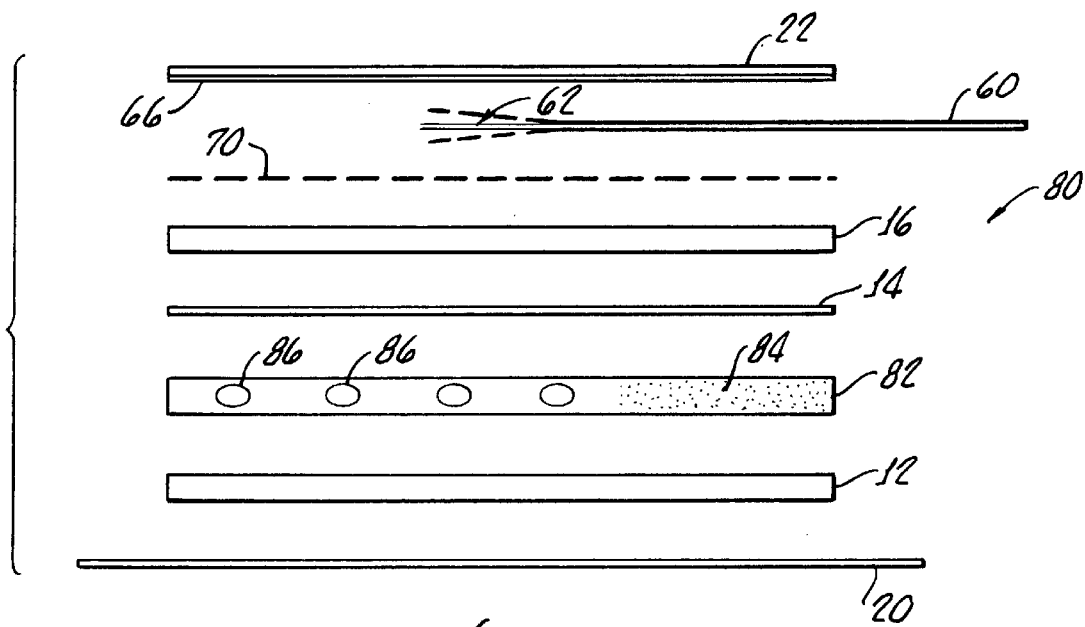
FIG. 5 is an alternative embodiment of the present invention similar to the embodiment shown in FIG. 4 but also including a medicament containing conductive polymerizable gel.

With reference to FIG. 5 there is shown yet another embodiment 80 in accordance with the present invention which utilizes a medicament containing conductive polymerizable gel layer 82 which may include a medicament 84 homogeneously incorporated into the gel 82 or contained in specific pockets 86 as shown in FIG. 5. Common reference characters refer to structural components which are substantially equivalent to the embodiment 50 shown in FIG. 4.

Although not specifically shown, the medicament 84 could also be incorporated into the first conductive gel 12. With application of electrical current, the electrode 80 is capable of introducing physiologically active ions into epidermis (not shown), and can be used in the treatment, for example of edema, ischemic skin ulcers, muscular pain, Peyronies disease, hyperhidrosis, arthritis, fungus infections, bursitis, and tendonitis. A theoretical synopsis of the mechanism of iontophoresis is not presented at this time.

Although there has been hereinabove described a specific medical electrode in accordance with the present invention for the purpose of illustrating the manner in which the invention may be used to advantage, it should be appreciated that the invention is not limited thereto. Accordingly, any and all modifications, variations, or equivalent arrangements which may occur to those skilled in the art should be considered to be within the scope of the present invention as defined in the appended claims.

What is claimed is:

1. A medical electrode comprising:
   a first conductive polymerizable gel layer for electrically coupling the electrode to a body:
      a flexible porous electrical conductor disposed on the first layer;
      a second conductive polymerizable gel layer disposed on said flexible porous electrical conductor and polymerized with the first layer through the porous conductor;
      an electrical connection disposed in contact with the second gel layer; and
      an insulative backing adhered to the second gel layer.

2. The medical electrode according to claim 1 wherein the second gel layer is more electrically conductive than the first gel layer.

3. The medical electrode according to claim 1 wherein said flexible porous conductor comprises a non-electrically conductive sheet with an electrically conductive layer disposed thereon.

4. The medical electrode according to claim 3 wherein the conductive layer is continuous across the sheet.

5. The medical electrode according to claim 3 wherein the conductive layer comprises an electrical grid.

6. The medical electrode according to claim 5 wherein said electrical grid comprises an electrically conductive ink pattern printed on said non-electrically conductive sheet.

7. The medical electrode according to claim 6 wherein the ink pattern includes a perimeter with interconnecting ink lines, said perimeter being set apart from edges of said non-electrically conductive sheet.

8. The medical electrode according to claim 7, wherein the second gel layer is more electrically conductive than the first gel layer.

9. The medical electrode according to claim 8 wherein said electrical connector comprises a snap connector, the snap connector extending through the backing for electrical access thereto.

10. The medical electrode according to claim 8 wherein said electrical connector comprises a lead wire.

11. The medical electrode according to claim 5 wherein said electrical grid is disposed over an entire surface of the sheet.

12. A medical electrode comprising:
   a first conductive gel layer for electrically coupling the electrode to a body:

a flexible porous electrical conductor disposed on said first conductive gel layer;

a second conductive gel layer disposed on said flexible porous electrical conductor and bonded to the first gel layer through the porous conductor;

an electrical connection disposed in contract with the second gel layer; and an insulative backing adhered to the second gel layer.

13. The medical electrode according to claim 12 wherein the second gel layer is more electrically conductive than the first gel layer.

14. The medical electrode according to claim 12 wherein said flexible porous conductor comprises a non-electrically conductive sheet with an electrically conductive layer disposed thereon.

15. The medical electrode according to claim 14 wherein the conductive layer is continuous across the sheet.

16. The medical electrode according to claim 14 wherein the conductive layer comprises an electrical grid.

17. The medical electrode according to claim 16 wherein said electrical grid compresses an electrically conductive ink pattern printed on said non-electrically conductive sheet.

18. The medical electrode according to claim 17 wherein the ink pattern includes a perimeter with interconnection ink lines, said perimeter being set apart from edges of said non-electrically conductive sheet.

19. The medical electrode according to claim 18 wherein the second gel layer is more electrically conductive than the first gel layer.

20. The medical electrode according to claim 16 wherein said electrical grid is disposed over an entire surface of the sheet.

21. The medical electrode according to claim 20 wherein said electrical connector comprises a snap connector, the snap connector extending through the backing for electrical access thereto.

22. The medical electrode according to claim 20 wherein said electrical connector comprises a lead wire.

23. A medical electrode comprising:

a conductive adhesive gel layer for electrically coupling the electrode to a body;

a flexible porous electrical conductor imbedded in said conductive adhesive gel layer, said flexible porous conductor comprising a non-electrically conductive sheet with an electrical grid disposed thereon, said electrical grid comprising an electrically conductive-ink pattern printed on said non-electrically conductive sheet;

an electrical connector disposed in contact with a surface of said conductive adhesive gel layer; and an insulative backing adhered to the gel layer surface.

24. The medical electrode according to claim 23 wherein the ink pattern includes a perimeter with interconnection ink lines, said perimeter being set apart from edges of said non-electrically conductive sheet.

25. The medical electrode according to claim 23 wherein said electrical connector comprises a snap connector, the snap connector extending through the backing for electrical access thereto.

26. A medical electrode comprising:

a first conductive polymerizable gel layer for electrically coupling the electrode to a body;

a medicament containing conductive polymerizable gel layer polymerized to the first conductive polymerizable gel layer;

a flexible porous electrical conductor disposed on the medicament containing gel layer;

a second conductive polymerizable gel layer disposed on said flexible porous electrical conductor and polymerized with the medicament containing gel through the porous conductor;

an electrical connector disposed in contact with the second gel layer; and an insulative backing adhered to the second gel layer.

27. The medical electrode according to claim 26 wherein a conductivity of the second gel layer is greater than a conductivity of the medicament gel layer and the first gel layer.

28. The medical electrode according to claim 26 wherein said electrical connector comprises a snap connector, the snap connector extending through the backing for electrical access thereto.

29. The medical electrode according to claim 26 wherein said electrical conductor comprises a lead wire.

* * * * *